United States Patent [19]
Parigi et al.

[11] Patent Number: 5,619,038
[45] Date of Patent: Apr. 8, 1997

[54] METHOD AND APPARATUS FOR DETERMINING THE POLYMER CONTENT OF A CELLULOSE/POLYMER MIXTURE AND ASSOCIATED CALIBRATION

[75] Inventors: John S. Parigi; Fred D. Patterson, III, both of Beaumont, Tex.

[73] Assignee: Temple-Inland Forest Products Corporation, Diboll, Tex.

[21] Appl. No.: 391,952

[22] Filed: Feb. 21, 1995

[51] Int. Cl.⁶ .......................... G01N 21/35; G01N 21/31
[52] U.S. Cl. .................. 250/339.12; 250/252.1; 250/304
[58] Field of Search ............ 250/339.12, 252.1, 250/304

[56] References Cited

U.S. PATENT DOCUMENTS

| | | | |
|---|---|---|---|
| 3,196,072 | 7/1965 | Wirtz | 162/198 |
| 3,498,719 | 2/1965 | Wing et al. | 356/36 |
| 3,585,106 | 9/1969 | Sepall et al. | 162/252 |
| 3,764,463 | 10/1973 | Histed et al. | 162/49 |
| 4,006,358 | 12/1977 | Howarth | 250/341 |
| 4,607,955 | 8/1986 | Corbett | 356/342 |
| 5,069,753 | 12/1991 | Nishi | 162/49 |
| 5,104,485 | 4/1992 | Weyer | 250/339.12 X |

FOREIGN PATENT DOCUMENTS 295486  12/1988  European Pat. Off. .......... 250/339.12

Primary Examiner—Carolyn E. Fields
Assistant Examiner—Edward J. Glick
Attorney, Agent, or Firm—Alton W. Payne

[57] ABSTRACT

A method and apparatus for determining and adjusting the polymer content of a cellulose/polymer blend prior to use in a paper-making machine. The method for evaluating a desired polymer contained in a cellulose/polymer mixture comprising the steps of acquiring a sample for evaluation from a cellulose/polymer mixture, dewatering the sample, shredding the dewatered sample, evaluating the shredded sample over the range of absorptances which correspond to the absorption characteristics of the desired polymer, determining a specific wavelength within the range which corresponds to a location of maximum absorbence and of low sensitivity with respect to spectral shifts, comparing the specific wavelength determined with standardized wavelengths representative of known polymer percentages, and determining the polymer content by selecting the standardized wavelength which best corresponds to the specific wavelength determined. The apparatus for evaluating a desired polymer contained in a cellulose/polymer mixture comprising a sampler, an agitator, a dewaterer, a shredder, a near-infrared spectrometer, a discriminator, a comparator and a selector.

28 Claims, 8 Drawing Sheets

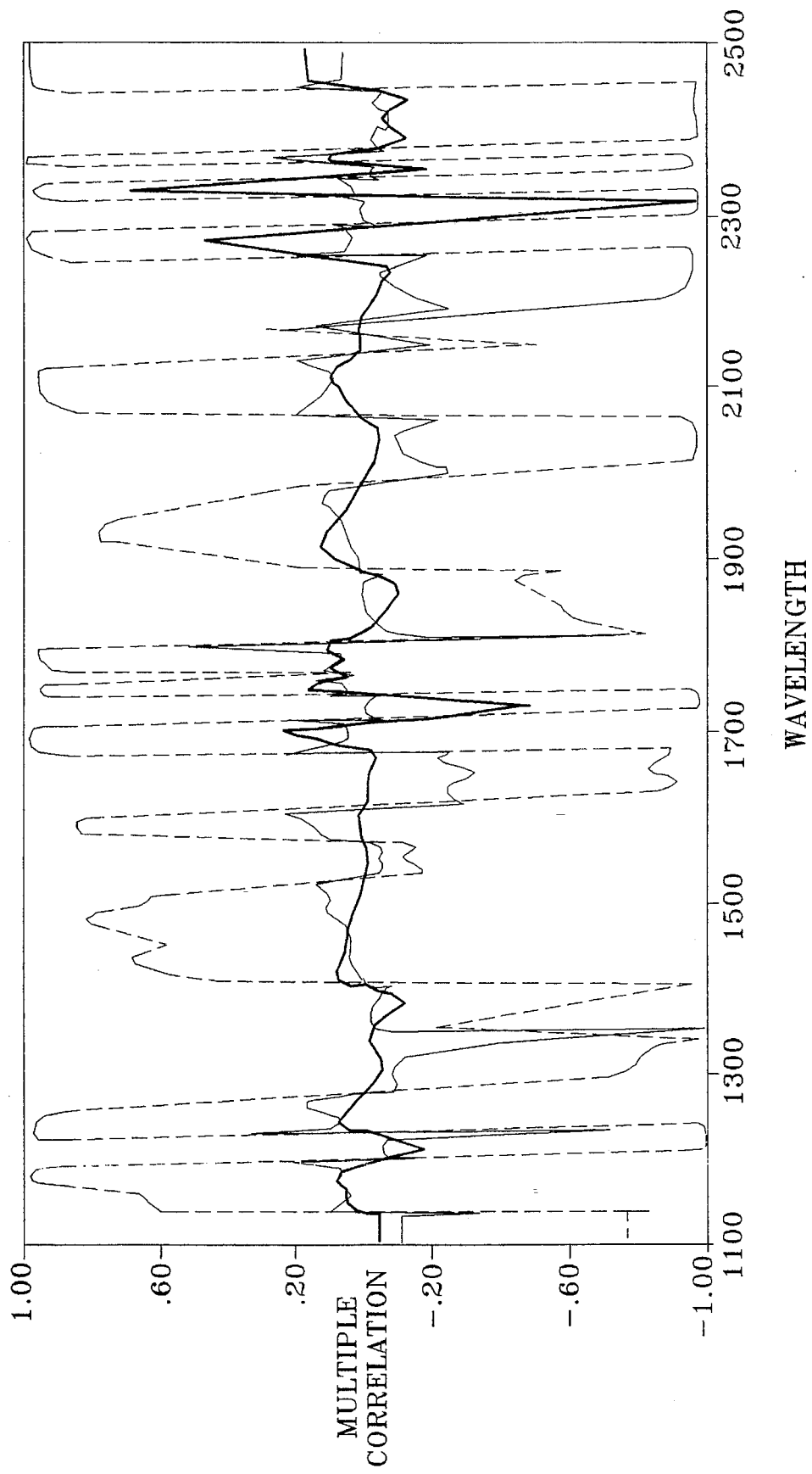

METHOD AND APPARATUS FOR DETERMINING THE POLYMER CONTENT OF A CELLULOSE/POLYMER MIXTURE AND ASSOCIATED CALIBRATION

FIELD OF THE INVENTION

The present invention relates generally to analyzing material prior to commercial processing. Primarily, the present invention relates to the paper making industry where raw materials are prepared prior to sending them to the paper machine, but applies equally well to other fields. Specifically, the present invention relates to a method and apparatus for determining the polymer content of a cellulose/polymer blend prior to use in a paper-making machine and also adjusting the polymer content.

BACKGROUND OF THE INVENTION

Cellulose/polymer mixtures are used to make a variety of products. For example, products made from a cellulose/polymer mixture range from food containers to building components. It is of extreme importance that the consistency, concentration or other physical property be accurately determined.

Cellulose is a complex carbohydrate, i.e., a polysaccharide, that forms the major part of the cell walls of all plants and is practically pure in the fibers of cotton, flax, jute, and ramie. Cellulose is insoluble in water and is rather inert chemically, although it may undergo reactions typical of the alcohols because each glucose unit has three hydroxyl (OH) groups. Paper is an impure cellulose derived from wood pulp, made by removing the lignin by one of several processes.

Polymers are large molecules that contain many repeating units, thus the formatives: poly=many and mer=units. Polymerization is the reaction in which small molecules react to form large molecules or polymers. Polymers have a wide use as plastics, finishes, and fibers. For a molecule, called a monomer, to form a polymer, it must have at least two reactive sites; that is, it must be difunctional. An example of a difunctional molecule is hydroxy acid. The hydroxyl (OH) group of one hydroxy acid monomer reacts with the carboxyl group (COOH) of another hydroxy acid monomer to form an ester (a dimer). The ester dimer is also difunctional and may react further to form a polyester, with multiple units in the polymer chain. It is appreciated by those skilled in the art that polymers may be formed in many ways to include many types of molecules. Typically, polymers are considered to have useful mechanical properties if they are of sufficiently high molecular weight.

In conventional practice, the polymer content of products made from cellulose/polymer mixtures was typically determined after the product was made or formed. Often, the polymer content of the final product was found to be unacceptable. Thus, the unacceptable products were rejected and ultimately sold for scrap, given away or otherwise disposed of.

In the pulp and paper processing industry, conventional testing and controlling devices do not provide for determining the polymer of a cellulose/polymer blend or mixture. The determination of the polymer content of a cellulose/polymer mixture in the pulp and paper processing industry has been, and continues to be, a significant problem. Determining the polymer content is typically inexact, time consuming and potentially hazardous.

Also, determining the polymer content of cellulose/polymer mixtures is subject to many variables. Variables which effect an accurate determination of the polymer content in such mixtures include temperature, reagent stability, moisture content, accurate chemical concentrations, sensitivity to physical parameters and the like. Achieving and maintaining a desired polymer content with respect to a process mixture of cellulose/polymer material is critical to manufacturing using such material. A preliminary determination of the polymer content is of critical importance since the resultant product would be defective with an incorrect polymer content.

Typically, the polymer content of cellulose/polymer mixtures can be determined using differential scanning calorimetry ("DSC"), gravimetric methods, and other analytical methods. The prior used methods have problems which must be overcome for their effective use. For example, with either differential scanning calorimetry or gravimetric methods, the temperature of the test is critical. Also in such prior known methods, the sample of cellulose/polymer mixture must have a weight which is precisely known. Still further, the prior known methods typically require a sample which is essentially free of all moisture. But still further, the use of differential scanning calorimetry or gravimetric methods typically takes in excess of thirty (30) minutes to determine the polymer content of a cellulose/polymer slurry sample causing considerable time delay.

Also of primary importance, some methods require the use of hazardous or corrosive materials. For example, the gravimetric method for determining polymer content of a cellulose/polymer mixture requires the use of cupriethylenediamine. The cupriethylenediamine used in the gravimetric method for determining polymer content is required to dissolve cellulose material. Cupriethylenediamine is hazardous in that it is a corrosive material which can cause burns and blindness upon contact. Yet still further, reagent stability causes additional concentration problems in trying to measure the polymer of a mixture.

It is, therefore, a feature of the present invention to provide a method and apparatus for evaluating a desired polymer of a cellulose/polymer mixture which is free from all the prior discussed problems associated with other methods and apparatus.

A feature of the present invention is to provide a method and apparatus for determining the polymer content in a mixture of polymer and cellulose.

Another feature of the present invention is to provide a method and apparatus that requires only a moist sample to determine the polymer content in a polymer/cellulose mixture.

Yet another feature of the present invention is to provide a method and apparatus which determines the polymer content of a polymer/cellulose mixture prior to the mixture being sent to the processor, paper-making machine or the like.

Still another feature of the present invention is to provide a method and apparatus for determining the polymer content of a polymer/cellulose mixture which avoids the use of hazardous chemicals which increases the probability of damage to property or harm to persons using prior known techniques.

Another feature of the present invention is to provide a method and apparatus for determining the polymer content of a cellulose/polymer mixture which is not sensitive to temperature or moisture as are other conventional methods.

A further feature of the present invention is to provide a method and apparatus for determining the polymer content of a cellulose/polymer mixture which is not sensitive to reagent stability or chemical concentrations as are other conventional methods.

Still another feature of the present invention is to provide a method and apparatus for determining the polymer content of a mixture before the mixture is used to create the end product, and thus, all potentially rejected material can be reused and converted into prime product.

Still another feature of the present invention is to provide a method and apparatus for determining the cellulose/polymer mixture which is exceedingly fast to implement and which decreases or totally eliminates all off quality product.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, a method and apparatus for evaluating a desired polymer of a cellulose/polymer mixture is provided.

A method for determining the concentration of a polymer in a cellulose/polymer mixture is provided. The steps of the method comprising acquiring a sample for evaluation from a cellulose/polymer mixture, conditioning the sample to assure it is homogeneous, dewatering the sample to remove excessive liquid from the sample, shredding the sample to the extent that the sample is in a fluffed state, scanning the sample to determine the absorption characteristics of the sample, and evaluating the sample absorption to determine the concentration of the sample in the cellulose/polymer mixture.

More particularly, the step of dewatering the sample to remove excessive liquid comprises the steps of engaging the sample with a strained shaker to drain liquid from the sample, engaging the sample with a sample press to drain liquid from the sample, and engaging the sample through a chamois wringer. The step of engaging the sample through a chamois wringer includes engaging the appropriate part of the chamois wringer with an absorbing medium, such as for example a paper towel, engaging the appropriate part of the chamois wringer with felt, and applying the sample through the chamois wringer so that the sample engages the absorbing medium and the felt. The step of scanning the sample to determine the absorption characteristics of the sample comprises the step of scanning the sample with a near infrared spectrometer. The step of evaluating the sample to determine the concentration of the sample in the cellulose/polymer mixture includes comparing the sample data achieved by scanning the sample with predetermined calibration data to determine the concentration of the sample in the cellulose/polymer mixture. Further, the step of acquiring a sample for evaluation includes determining the amount of acquired sample to yield a specific volume of desired product. The step of evaluating the sample absorption includes comparing the sample absorptance with the absorptance of standards representative of known polymer percentages. The step of comparing the sample absorptance with the absorptance of standards representative of known polymer percentages includes additionally comparing the respective absorptances between the range of approximately 1630 to 1770 nanometers. Also, the step of comparing the respective absorptances between the range of approximately 1630 to 1770 nanometers comprises the step of comparing the respective wavelengths at about 1728 nanometers.

More particularly, the method for determining the concentration of a polymer in a cellulose/polymer mixture includes the steps of calculating the quantity of additional polymer needed to achieve the desired cellulose/polymer mixture adding the polymer as needed, and releasing the resultant cellulose/polymer mixture for use.

In a related embodiment of the present invention, the method for determining the concentration of a polymer in a cellulose/polymer mixture is provided with the mixture having characteristic carbon-hydrogen stretching frequencies. The steps for determining the concentration of a polymer in a cellulose/polymer mixture include dewatering a sample from the cellulose/polymer mixture to remove excessive liquid from the sample, shredding the sample to the extent that the sample is in a fluffed state, scanning the sample using spectroscopy, determining the absorption characteristics of the sample at a specific wavelength to generate a sample absorption such that the sample absorption is related to the characteristic carbon-hydrogen stretching frequency associated with the mixture, comparing the specific sample absorption obtained with standards representative of known polymer percentages, and evaluate the sample for determining the concentration of the polymer in the cellulose/polymer mixture.

More particularly, the step of determining the absorption characteristics of the sample at a specific wavelength to generate a sample absorption includes determining the absorption at a range of approximately 1690 to 1770 nanometers. Also, the step of determining the absorption characteristics of the sample at a specific wavelength to generate a sample includes determining the absorption at a range that falls within the first overtone C–H absorbency range of approximately 1630 to 1750 nanometers.

In another embodiment, a method for determining the concentration of a polymer in a cellulose/polymer mixture includes the steps of mixing the cellulose/polymer mixture to assure homogeneity, acquiring an appropriate sample, dewatering the sample to remove excessive liquid therefrom, shredding the sample to the extent that the sample is in a fluffed state, evaluating the sample using spectrometry to determine the absorption characteristics of the sample, and comparing the absorption characteristics of the sample with absorption of known polymer percentages to obtain the polymer concentration of the sample.

In yet another embodiment of the present invention, an apparatus is provided for determining the concentration of a polymer in a cellulose/polymer mixture for use in fabricating products from the mixture. The primary components of the apparatus consists of means for acquiring a predetermined amount of sample, means for agitating the sample, means for dewatering the sample, means for shredding the sample, a near-infrared spectrometer for evaluating the shredded sample, means for determining a specific absorptance within a range which corresponds to a location of maximum absorptance and of low sensitivity with respect to spectral shifts, means for comparing the specific absorptance determined with standardized absorptances representative of known polymer percentages, and means for determining the polymer content. The means for acquiring a predetermined amount of sample for evaluating the cellulose/polymer mixture provides that the sample is calculated to yield a specific weight of desired product. The near-infrared spectrometer evaluates the shredded sample over the range of absorptances which correspond to the absorption characteristics of the desired polymer. Preferably, the shredded sample is placed into a sample cell such that the sample completely fills the cell. The means for determining a specific absorptance within a range which corresponds to a location of maximum absorptance and of low sensitivity with respect to spectral shifts may further provide the use of a second derivative test concerning the range of absorptances. The means for comparing the specific absorptance determined for the sample with standardized absorptances representative of known polymer percentages also may provide for comparing the absorbence determined by the second derivative of the range of absorptances associated with the sample to the absorbences determined by the second derivative of known polymer standards bearing specific polymer percentages. More particularly, the comparison may be made between the range of 1630 to 1770 nanometers.

In association with and as a part of the present invention, a method for calibration for use in determining the concentration of a polymer in a cellulose/polymer mixture is provided. The steps of the calibration include selecting a plurality of concentrations spread over a preselected concentration range, preparing a standard sample for each selected concentration, blending each prepared standard sample with water, dewatering each mixed standard sample, shredding each dewatered standard sample, analyzing each shredded standard over the instrument range for wavelengths which correspond to the absorption characteristics of the desired polymer for generating spectral absorption data for each sample, evaluating the respective spectral absorption data to determine maxima and minima absorption values for generating max/min data for each sample, evaluating the max/min data to determine its appropriateness for use to analyze unknown samples containing the desired polymer, and selecting the max/min data associated with a multiple-R correlation test that corresponds to the appropriate C–H absorbance and has non-sensitive characteristics.

More particularly, the calibration method includes selecting a plurality of concentrations spread over a preselected concentration range which may include using five or more selected concentrations differing by approximately two percent (2%). A standard sample is prepared for each selected concentration by weighing a plurality of portions of dry pulp and weighing a plurality of portions of dry polymer. The weight or mass of the respective pulp and polymer portions are selected to achieve the desired ratio. Each shredded standard is evaluated over the instrument range for wavelengths which correspond to the absorption characteristics of the desired polymer to generate spectral absorption data for each sample. The standardized samples are analyzed over the preselected concentration range for the desired polymer such that the preselected concentration range provides for wavelengths which correspond to the absorption characteristics of the desired polymer. Spectral absorption data is generated for each standardized sample such that the spectral information is collected on an associated computer. The analysis includes obtaining spectral data over a range of 1,100 to 2,500 nanometers, and preferably selecting a specific wavelength of approximately 1728 nanometers. The step of evaluating the respective spectral absorption data to determine maxima and minima absorption values for generating max/min data for each sample also includes determining the maxima and minima absorption values for each sample and evaluating them using a second derivative test. The second derivative test comprises fitting spectral data over the range of 1,100 to 2,500 nanometers, and fitting the spectral data about the 1728 nanometers value.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

FIG. 7 is a graph illustrating a typical multiple correlation curve of wavelength versus correlation, sensitivity and spectrum data associated with practicing the present invention.

Figure 1:
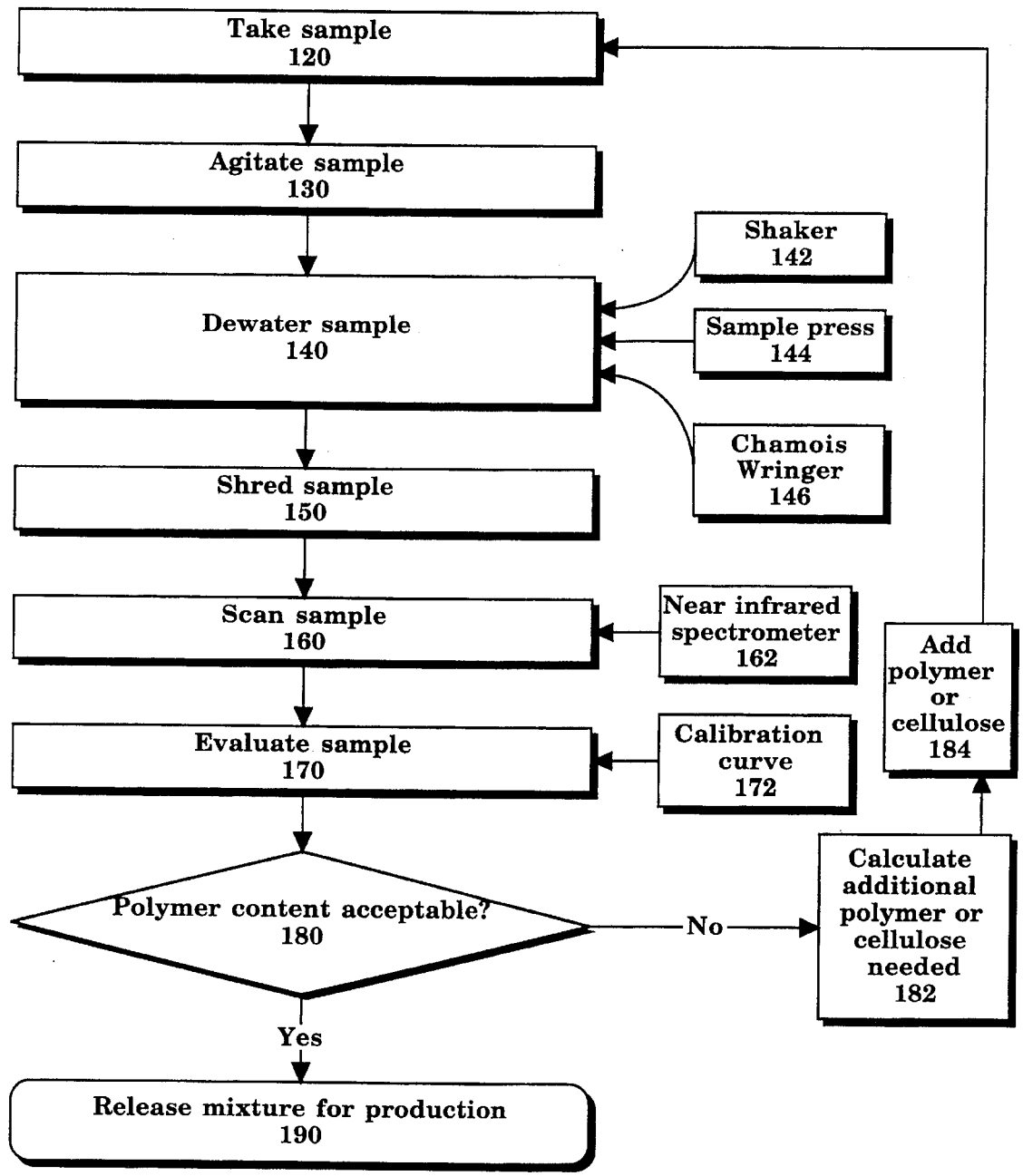
FIG. 1 is a flowchart illustrating a preferred embodiment for determining and adjusting the polymer content of a cellulose/polymer blend using the present invention in a production plant.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

A basic understanding of spectroscopy is required for an appreciation of the present invention. Different materials absorb or emit electromagnetic radiation to varying extents, depending on their electronic structure. Therefore, studies of the electromagnetic spectrum of a material yield scientific information. Such studies are collectively known as spectroscopy. They are used for research and analysis in many fields, including chemistry, physics, astronomy, biology and medicine. Many spectroscopic methods are appropriate for use in the present invention and may be based upon the exposure of a sample to electromagnetic radiation. Measurements are then made of how the intensity of radiation absorbed, emitted, or scattered by the sample changes as a function of the energy, wavelength, or frequency of the radiation.

Characteristic arrays of lines are given off by different chemical elements. For example, incandescent sodium always yields certain yellow lines near the middle of the spectrum, and no other element gives these lines. Thus when these lines appear, sodium must be present in the incandescent substance. If the lines are bright, the light has come directly from the incandescent sodium. If the lines are dark, the light has passed, somewhere along its path, through an absorbing vapor containing some gaseous sodium. Since only minute quantities of an element are needed to make its lines appear, such analysis is very accurate quantitatively. This makes it possible to identify the elements in unknown substances. Scientists have obtained spectra corresponding to the different elements and have measured and charted essentially every line. For example when the composition of a star is sought, a photograph of the star's spectrum is taken and the associated lines of the spectrum are compared against the charts for the elements to determine the composition of the star.

These spectra can be understood using a very simple model. An atom can be considered to consist of an electron revolving like a "planet" around a central nucleus, or "sun." As an atom absorbs energy, for example by being heated, this orbit would enlarge by definite amounts, each enlargement representing the absorption of one quantum, or "packet," of energy. When energy is emitted, as in the form of light, the electron would fall by steps into inner orbits, and the frequency of the light would depend upon how many orbits were traversed. If the electron fell inward by one orbit, the "energy splash" resulting from the falling electron would travel outward as light of a certain frequency. If the electron fell inward by two orbits, light of a different frequency would be emitted. Such a view was appropriate for atomic analysis, but molecular analysis is much more difficult.

Molecules that consist of many atoms have very complex vibrations. For example, the simple water molecule has three different modes. In a more complicated molecule such as acetone, with 10 atoms, 24 modes of vibration are possible. Fortunately, not all vibrational modes are important for identifying molecular structures. For example, the most distinct vibration of the acetone molecule is that of the carbonyl (C–O) group. The rest of the acetone molecule can be regarded as fixed in position. The absorption frequency of the carbonyl group is not strongly influenced by the rest of the molecule, so that most compounds that contain this group have a similar band in their infrared (IR) or Raman spectra, or both, at frequencies between 5.0 and $5.6 \times 10^{13}$ frequencies per second, or Hertz (Hz). It is common to express these frequencies in terms of the wave number, or number of wavelengths per centimeter. This is found by dividing the frequency by the speed of light, c, which is $3 \times 10^{10}$ cm/sec.

The development of vibrational infrared (IR) absorption spectroscopy was a major step in applying molecular spectroscopy to determine molecular structure. The IR spectrum, and the complementary scattering spectrum called the Raman spectrum, provide information about vibrations of atoms with respect to each other, the most important vibrations being the mutual vibrations of two bonded atoms. Vibrations of larger fragments of a molecule are less important for identifying molecular structures. In IR spectroscopy, the two vibrating atoms are regarded as two point masses connected by a spring representing the bond between the two atoms. The frequency of the vibration corresponds to the frequency of the absorbed radiation, and it depends on the masses of the atom and the bond strength. This frequency is characteristic of the two atoms and is practically independent of the rest of the molecule. Many chemical groups can be recognized from a vibrational spectrum, doing away with the need for conducting more complicated and time-consuming qualitative chemical analysis.

The existence of group frequencies makes IR and Raman spectroscopy valuable for analysis. An important group frequencies are those which correspond to light hydrogen atoms (H) vibrating with respect to the rest of the molecule, and to vibrations of double and triple bonds.

FIG. 1 is a flowchart illustrating a preferred embodiment of the present invention. FIG. 1 is exemplary of an analytical method or apparatus to determine and adjust the polymer content of a cellulose/polymer mixture. The cellulose/polymer mixture could, for example, be held in a raw material preparation area prior to the mixture being sent to a processing machine. A typical processing machine might be, for example, a paper-making machine.

As illustrated in FIG. 1, a sample is taken 120. It is preferable to have a sample that is homogeneous. The cellulose/polymer mixture or blend may be mixed vigorously or some other technique may be used to achieve homogeneity. Typically, the sample is agitated to assure that homogenous distribution and representative sampling is present.

The sample is dewatered 140. The dewatering can be accomplished by using any dewatering device as can be appreciated by those skilled in the art. However, it has been found that a strained shaker 142 is an appropriate dewatering device. The shaker 142 can be used to drain excessive liquid from the sample. Also, it has been found that a sample press 144 is advantageous in the dewatering process. Particularly, a brass sample press 144 has been used to effectively assist in dewatering for the present invention. Still further, it has been found that the use of a chamois ringer 146 is effective as a final dewatering process. For example, the sample may be placed between paper towels and felt. The layered combination of paper towels, sample and felt can be slowly passed through the chamois ringer 146. It has been found that the sample is sufficiently dewatered after two or three passes through the chamois ringer. Although the presently preferred description describes a three-tier dewatering process, more steps or fewer steps may be appropriate depending on the particulars of the situation.

The dewatered sample is then shredded 150. Preferably, shredding is accomplished by using a blending device. The presently preferred way of shredding the sample is to tear the sample into small pieces. The small pieces are placed in a blender jar which is activated to shred the sample. The sample is sufficiently shredded when none of the torn pieces remain intact and the sample has become "fluffed." It has been found advantageous that the shredding be interrupted several times for manual repositioning of the shredded pieces within the blender jar. Those skilled in the art can appreciate that other shredding techniques may be equally appropriate, or even better, in specific situations.

The shredded sample is then scanned 160. The presently preferred scanning method is to use a near-infrared spectrometer 162. Prior to the scanning, the shredded sample, in its entirety, is placed into a sample cell for use with the near-infrared spectrometer. It is important that the original sample collected be of adequate size to completely fill the sample cell. Also, the sample is required to make sufficient contact with the optic configuration of the near-infrared spectrometer 162. The sample cell is packed to assure a uniform surface beneath the cell window. Preferably, no deviation in sample size is allowed once the appropriate sample size for the sample cell is determined. The sample is scanned using the near infrared spectrometer.

The sample is evaluated 170. The evaluation of the sample 170 provides a way of determining the polymer content in the sample. Although the evaluation may be done in numerous ways, the present preferred technique is to utilize a calibration curve 172. Thus, the polymer content is determined by comparison of the scanned data to a calibration curve. The calibration curve is discussed in detail later herein.

The description of the invention embodied in FIG. 1 can be used in may different forms of analysis. For example, the description of the invention in FIG. 1 can be used for finished product analysis. Also, the application of the invention described in FIG. 1 can be used for pre-manufacturing analysis, as previously discussed.

FIG. 1 also illustrates the application of the present invention specifically for determining the polymer content of the starting material before the mixture is released for production. The polymer content of the mixture can be tested to determine if it is acceptable 180. If the polymer content is acceptable, the mixture can be released for production, for example, to a paper-making machine. If the polymer content is not acceptable, then a calculation must be made to determine the amount of polymer or cellulose needed to make the mixture acceptable 182. Once the appropriate amount of cellulose or polymer needed is calculated, the polymer or cellulose can be added to the mixture 184. The new mixture is repeated through the above-discussed procedure described until the correct concentration is achieved.

Although the prior discussion has been limited to specific steps, the steps can be automated without varying from the scope or content of the present invention. It is appreciated that one or more devices, now known or yet to be developed, can be adapted to practice the present invention. Automation can readily be applied to the details as described.

Figure 2:
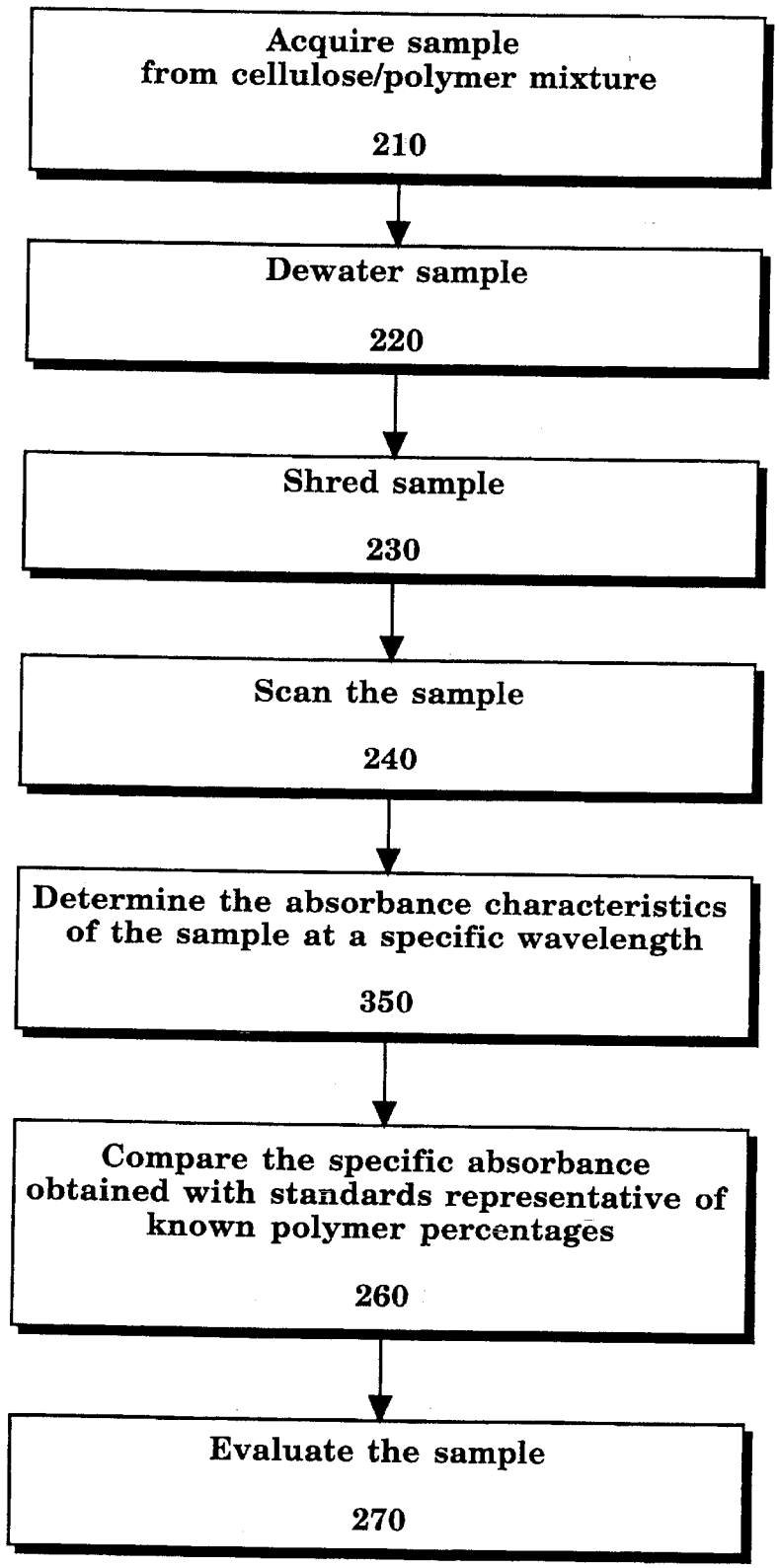
FIG. 2 is a flowchart illustrating a preferred method encompassed by the present invention for determining the polymer content of a cellulose/polymer blend.

FIG. 2 is a flowchart illustrating a preferred method encompassed by the present invention. FIG. 2 describes a method which utilizes the absorption characteristics of the polymer material at a specific wavelength for determining the acceptability of the mixture. A sample is acquired from a cellulose/polymer mixture 210. The sample is dewatered 220. The dewatering process can be any process known for dewatering the respective sample. Examples of preferred dewatering processes are illustrated and discussed in FIG. 1 with respect to the shaker 142, the sample press 144 and the chamois ringer 146. All dewatering devices that are known readily to those skilled in the art are applicable, as well as those yet to be developed. The sample is then shredded 230. As with the prior discussion of FIG. 1, the shredding can be accomplished by any conventional means currently known, or yet to be developed.

An important step of the method illustrated in FIG. 2 is determining the absorbence characteristics of the sample at a specific wavelength 350. The actual wavelength used for the presently preferred embodiment of the present invention is 1728 nanometers. The wavelength of 1728 nanometers is used because this wavelength is representative of the C–H stretching frequencies associated with the cellulose/polymer mixture. This is represented by the multiple correlation plot of FIG. 8. Preferably, the nonsensitive areas are used. The nonsensitive areas provide that wavelength shifts and other instrument variables, such as for example slight temperature changes, have little or no impact on measurement accuracy. Thus, the accuracy of the present invention is greatly enhanced. The wavelength range of approximately 1690 to 1770 nanometers is preferred. The cited range and specific value have been found to provide enhanced effectiveness in practicing the present invention. Further, the 1690 to 1770 nanometer range falls within the first overtone C–H absorbency range of approximately 1630 to 1750 nanometers. It is believed that such values provide enhanced results because the polyethylene molecule is composed of C–H bonds. Thus, FIG. 2 emphasizes using a specific wavelength at which the absorbence characteristics can be determined. It can be appreciated that any many wavelengths may be appropriate although the present preferred embodiment of the invention is to use approximately 1728 nanometers.

Figure 3:
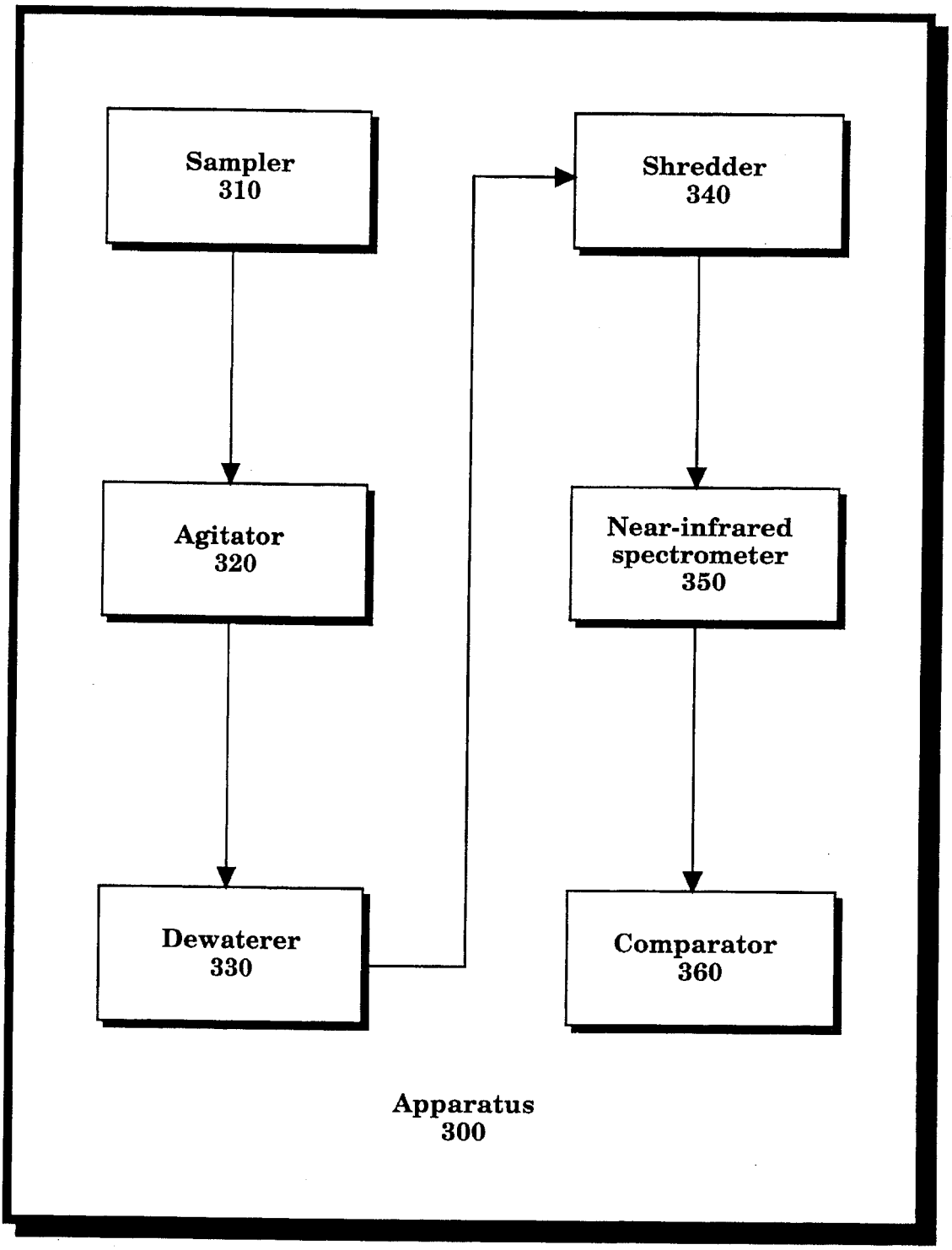
FIG. 3 is a block diagram illustrating a preferred embodiment of the apparatus of the present invention for determining the polymer content of a cellulose/polymer blend.

FIG. 3 is block diagram illustrating a preferred embodiment of the apparatus 300 of the present invention. The apparatus 300 of the present invention comprises a sampler 310, an agitator 320, a dewaterer 330, a shredder 340, a near-infrared spectrometer 350 and a comparator 360. The sampler 310 can be any sampling device for achieving a homogenous sample. For the present preferred embodiment, the agitator 320 should provide for vigorous agitation of the cellulose/polymer mixture acquired by the sampler 310. The dewaterer 330 provides that sufficient aqueous solution is removed from the sample. Examples of dewaterers are provided above. The shredder 340 can be any conventional shredding device appropriate for the dewatered sample used in the apparatus 300. The near-infrared spectrometer 350 can be a spectrometer which is commercially available. For example, the present used near-infrared spectrometer is one manufactured by NIRSystems having model number 5000.

Other instruments can be used to achieve the same result as that achieved by the preferred near-infrared spectrometer. Particularly, a spectrophotometer can be used. A spectrophotometer is an optical instrument for comparing the composition and intensity of light with light from another source. When a substance is burned in a flame, the light emitted contains wavelengths of light that are specific for the elements of the substance. A flame spectrophotometer can be used to analyze this light and identify and quantitate the elements. The absorbence spectrophotometer is widely used in all analytical laboratories to identify and quantitate substances in solutions. In routine chemical analysis, only one substance is analyzed at a time by a beam of monochromatic light directed through the sample. The wavelength is selected to be one that the solute absorbs strongly but that other components in the solution do not absorb. The concentration of the solute is calculated from the absorbence of the light by comparing it to the absorbence of a standard solution. For example, the color of paint can be exactly defined using a reflective spectrophotometer that measures the bands of colors in the spectrum of light reflected from a painted surface.

Figure 4:
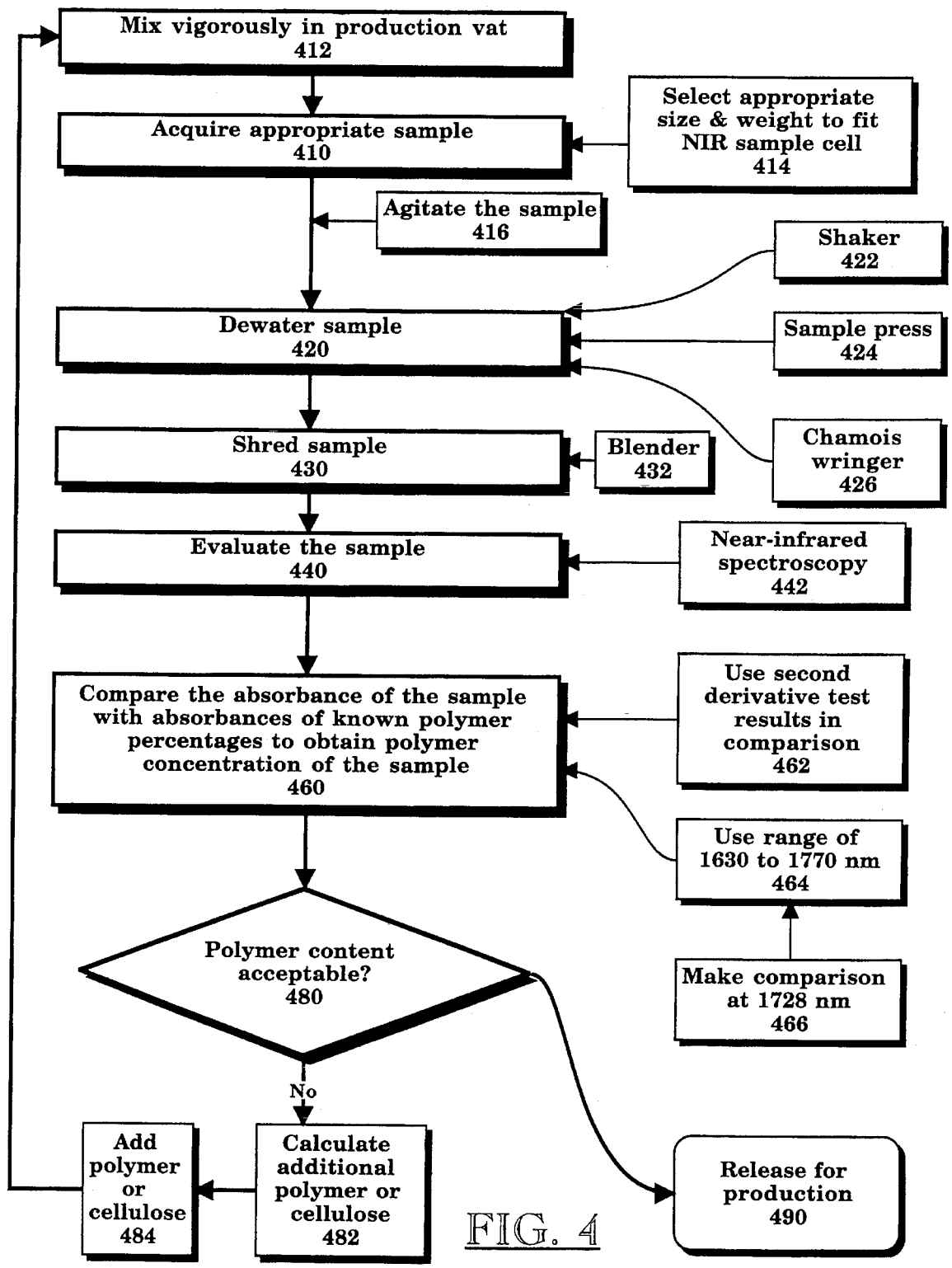
FIG. 4 is a flowchart illustrating the details of a preferred embodiment of the method of the present invention for determining and adjusting the polymer content of a cellulose/polymer blend.

FIG. 4 is a flowchart illustrating a preferred embodiment of the method or apparatus of the present invention. Prior to acquiring the sample 410, the cellulose/polymer mixture may be vigorously mixed 412. Also prior to acquiring a sample 410, the sample may be correlated to a specific weight of end product 414. The sample is acquired 410. The optionally mixed and correlated sample may be agitated 416. The acquired sample 410 is then dewatered 420. The dewatering devices which have been used in the present invention include, but are not limited to, a shaker 422, a sample press 424 and a chamois ringer 426. It can be appreciated that many other known dewatering procedures may be equally applicable, as previously discussed. (Also see, FIG. 1) The dewatered sample is shredded 430. It can be appreciated that any shredding procedure or device is appropriate. The sample is evaluated 440. The preferred evaluation technique used in the present invention is near-infrared spectrometry 442. The optional technique of correlating the sample to a specific weight of end product 414 is associated with the technique of using near-infrared spectrometry 442.

As previously discussed, absorption is related to the physical or chemical properties of a substance. Absorbence is the penetration of a substance into the body of another, and most notably is known as, radiant energy being transformed into other forms, such as for example heat, by passing through a material substance. Each substance may be considered to have an absorption measured by the fraction of the radiant energy falling upon the substance which is absorbed or transformed, i.e., the ratio of absorbed to incident radiation. Absorptance may sometimes be referred to as absorptivity or absorptive power. Absorptance is related to the particular substance. More particularly, absorptance has been found to be proportional to the amount, quantity or mass of a substance. However, additional controls are required to provide accurate determinations about a substance. For example, the spectrum of transmitted light of a solid or liquid absorbing substance shows broad dark regions which are not resolvable into lines and have no sharp or distinct edges. To only measure absorptance, without more, is unproductive and results in questionable information. The present invention avoids such problems. The present invention avoids these problems by using a particular wavelength or range of wavelengths. The wavelength, or range thereof, used is identified with physical or chemical properties of the substance under investigation, for example polyethylene. Thus, it is preferable that a specific wavelength is used. The specific wavelength is associated with a physical or chemical property of the sample. The specific wavelength in the preferred embodiment is associated with the first overtone C–H absorbency of the polymer in the sample. A comparison of the absorbence of the sample with absorbences of known polymer percentages is used to determine the polymer concentration of the sample 460.

A specific wavelength associated with the absorbence of the sample is identified preferably with a second derivative test 462. The wavelength associated with the absorbence as identified using the second derivative test 462, and the absorbence is compared with the standardized absorbences representative of known polymer percentages 460, 464, 466. Further, the standardized absorbences and associated wavelengths are determined for a specific range with respect to polyethylene. The wavelength range for polyethylene absorbence is 1630 to 1770 nanometers 464. The specific comparison is made for polyethylene at a wavelength of 1728 nanometers 466. The polymer content is then selected. The selection is based upon the comparison of absorbences as determined by the comparison of the specific wavelength and the standardized wavelengths.

After the polymer content is selected by comparison 460, the polymer content must be evaluated to determine if it is acceptable 480. If the polymer content is acceptable, then the mixture of polymer and cellulose may be released for production 490. If the polymer content is not acceptable, then a calculation must be made 482. The calculation determines the additional polymer or cellulose which must be added to make the polymer content acceptable. After the calculation is made, the polymer or cellulose is added 484. The technique illustrated in FIG. 4 is then applied to the new polymer/cellulose mixture, and so forth, until a mixture with an acceptable polymer content is achieved.

The second derivative test 462, as discussed with respect to FIG. 4, is the usual second derivative test for determining a relative maximum or a relative minimum. The second derivative test has been found to be appropriate for use in the present invention. Several assumptions must be made in using the second derivative test. First, the function to which the second derivative test is applied must have two derivatives. Also, the second derivative must be continuous. Lastly, the point of investigation, $X_0$, must be a critical point. A critical point is defined as the point where the first derivative equals zero. The functions utilized in the present invention, all comply with the assumptions required for the second derivative test. Thus, if the value of the second derivative at the critical point is greater than zero, the function has a relative minimum at the critical point. If the value of the second derivative at the critical point is less than zero, the function has a relative maximum at the critical point. If the value of the second derivative at the critical point equals zero, the second derivative is indeterminate because the critical point may also be a point of inflection. A point on a curve is a point of inflection if the value of the second derivative at the critical point is equal to zero and a graph of the function is concave upward on one side and concave downward on the other side. Thus, no maximum or minimum exists.

Figure 5:
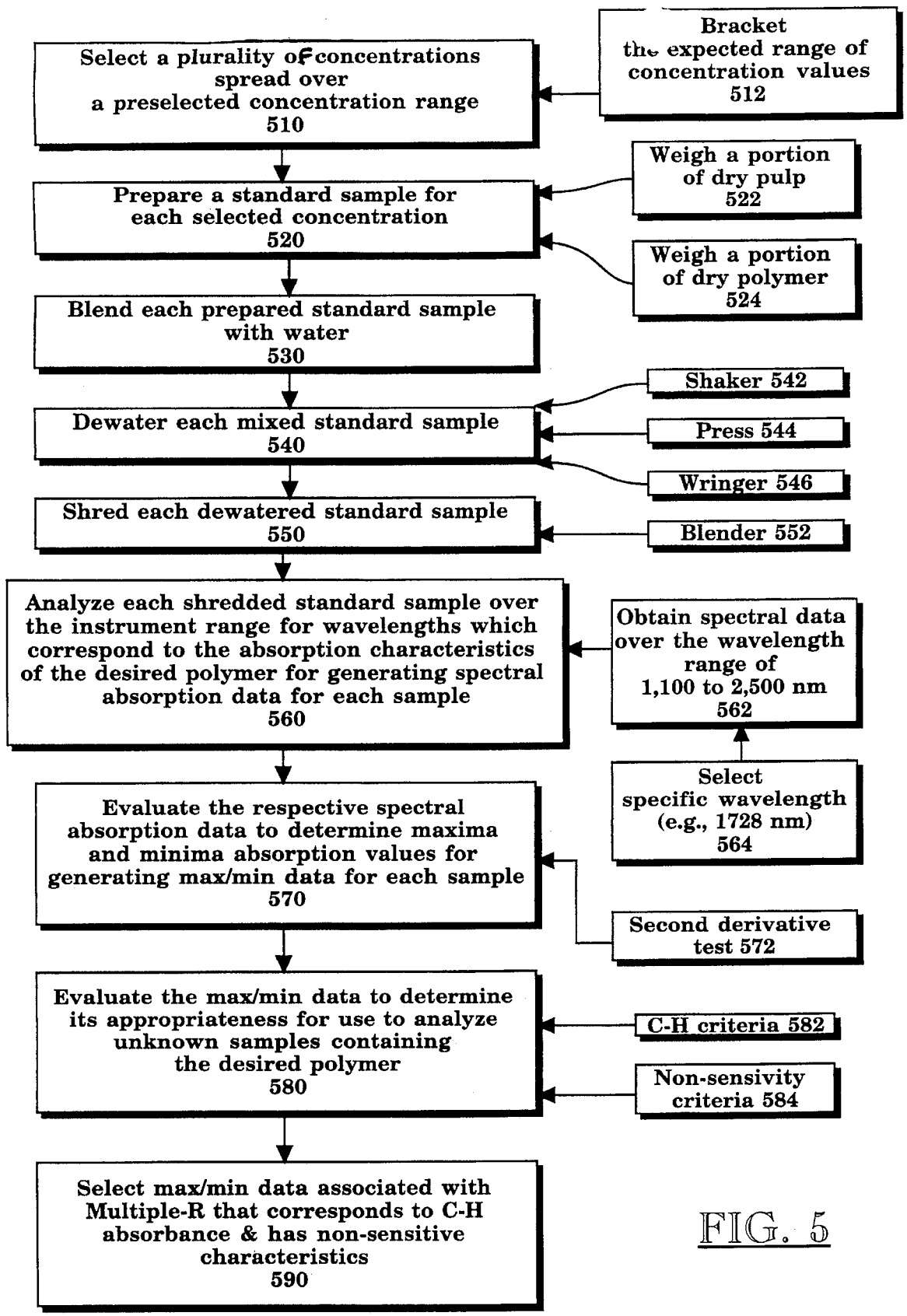
FIG. 5 is a flowchart illustrating a detailed embodiment of the calibration method of the present invention used in association with determining and adjusting the polymer content of a cellulose/polymer blend.

A preferred method of calibration for the present invention is illustrated in FIG. 5. A selection is made of a plurality of concentrations spread over a preselected concentration range 510. The concentration range is chosen based upon the end product values sought. A plurality of concentrations should be used. It has been found that five (5) or more selected concentrations yields good results. Also, it has been found that concentrations differing by approximately two percent (2%) yields good results. The expected range of concentration values is determined. The number of concentrations are selected to bracket or cover the entire expected range 512. Obviously, the more points selected, the greater the statistical accuracy which is expected to be achieved in the calibration.

One or more samples are prepared 520. A sample is prepared for each selected concentration, thus typically, a plurality of samples are prepared. The standardized samples for each selected point in the expected range are made by accurately weighing dry portions of polymer and pulp. For example, a 25% polymer standard will contain one gram of dry polymer and three grams of dry pulp. Thus, a mass of dry pulp 522 and a mass of dry polymer 524 are measured for each standard sample.

Each standard sample prepared is blended 530. For the preferred embodiment, the prepared sample is blended with water 530. The polymer/pulp standard sample is placed in a Waring Blender jar, for example. The Waring Blender jar is filled approximately half full of water. The standardized sample is blended 530, preferably in the jar.

The standardized sample is then dewatered 540. The dewatering process can be as previously discussed. The dewatering can be accomplished by using any applicable dewatering device. A shaker 542 that is strained has been found to be an appropriate dewatering device. The shaker 542 can be used to drain excessive liquid from the standardized sample. Also, it has been found that a sample press 544 is advantageous in the dewatering process. Particularly, a brass sample press 544 has been used to effectively assist in dewatering for the calibration of the present invention. Still further, it has been found that the use of a chamois ringer 546 is effective as a final dewatering process or means. The standardized sample may be placed between paper towels and felt. The layered combination of paper towels, standardized sample and felt can be slowly passed through the chamois ringer 546. It has been found that the standardized sample is sufficiently dewatered after two or three passes through the chamois ringer. The presently preferred embodiment describes a three-tier dewatering process or the use of three devices. It can be appreciated that more or fewer steps, or devices, may be appropriate depending on the particulars of the situation.

The dewatered standardized sample is shredded 550. The shredding procedure for the calibration method of the present invention provides that the respective standardized samples are cut or torn into small pieces of approximately one to two square centimeters. The cut pieces are placed in a small stainless steel blender jar 552. The pieces are shredded until none of the larger pieces remain. Typically, the shredding 550 will need to be interrupted for manually repositioning the pieces within the blender jar 552.

Each shredded standardized sample is then analyzed 560. The analysis of the standardized sample is performed over the preselected concentration range of the desired polymer. The preselected concentration range provides for wavelengths which correspond to the absorption characteristics of the desired polymer for generating spectral absorption data for each standardized sample. The presently preferred analysis uses a near-infrared spectrometer. The entire shredded standardized sample is placed into a standard sample cell of the near-infrared spectrometer. It is important that the cell is completely filled. The completely filled cell ensures a uniform surface beneath the cell window for a more accurate measurement using the near-infrared spectrometer. The near-infrared spectrometer is used to scan the standardized sample. The spectral information is collected on an associated computer. The analysis 560 includes obtaining spectral data over a range of 1,100 to 2,500 nanometers 562 and selecting a specific wavelength 564, for example, the wavelength of 1728 nanometers for polyethylene.

The respective spectral absorption data is evaluated 570. The evaluation determines the maxima and minima absorption values. A determination of the maxima and minima absorption values generates max/min data for each sample. The max/min data is evaluated using a second derivative test 572. The second derivative test 572 includes fitting spectral data over the range of 1,100 to 2,500 nanometers and fitting the spectral data about the 1728 nanometer value.

The maxima and minima absorption values are evaluated 580. The evaluation is to determine the appropriateness of using the data as a standardized sample to compare unknown samples. Although other criteria are appropriate, it has been found for the present preferred embodiment of the invention, a C–H criteria 582 and a non-sensitivity criteria 584 are appropriated. Applying both the C–H criteria 582 and the non-sensitivity criteria 584 achieve enhanced results.

The best maxima and minima absorption data is selected 590. A regression analysis is performed on the second derivative data. The regression analysis covers the wavelength range of 1,100 to 2,500 nanometers. A multiple regression curve is generated. (See, FIG. 7) A sensitivity curve is generated. (See, FIG. 8) The sensitivity is overlaid with the multiple regression curve. An area of low sensitivity is sought. Areas of low sensitivity minimize the effects of spectral shifts among other things, moisture, temperature, etc. For example with respect to polyethylene, the area of low sensitivity occurs at approximately 1714–1735 nanometers. The regression analysis is recalculated at the selected wavelength, for example with respect to polyethylene at 1728 nanometers. The suitability of the regression analysis is determined. The determination of the suitability of the regression results is accomplished by studying a residual plot (See, FIG. 9), the value of the correlation coefficient and the actual plot of the calibration curve. Typically, the residual plot illustrates the difference between the actual lab value of the standard and the value generated by the calibration curve. When the results are considered suitable, the calibration equation is saved and used for sample determination with the general methodology of the present invention.

Figure 6:
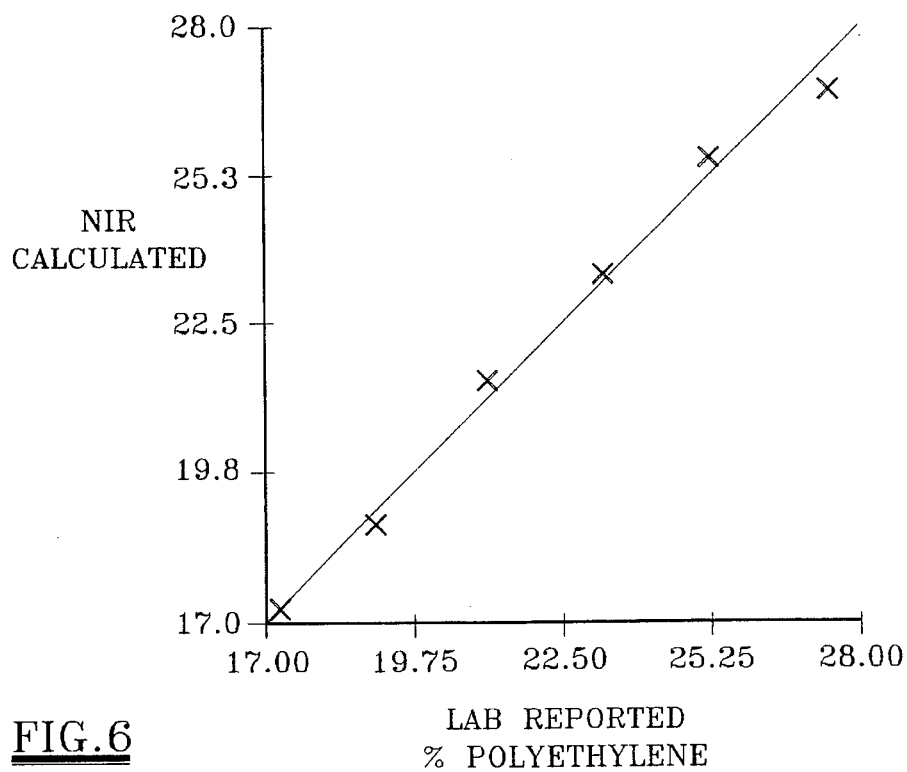
FIG. 6 is a graph illustrating a typical curve of empirical data versus calculated data associated with practicing the present invention.

FIG. 6 is a graph illustrating the empirical data on the abscissa and the calculated data on the ordinate. The curve illustrated in FIG. 6 is for polyethylene. It can be appreciated from the curve that the calibration is extremely accurate.

FIG. 7 is a graph illustrating a typical multiple correlation plot, as previously discussed, for use with the present invention. FIG. 7 illustrates a plot of wavelength versus correlation, sensitivity and spectrum data.

Figure 8:
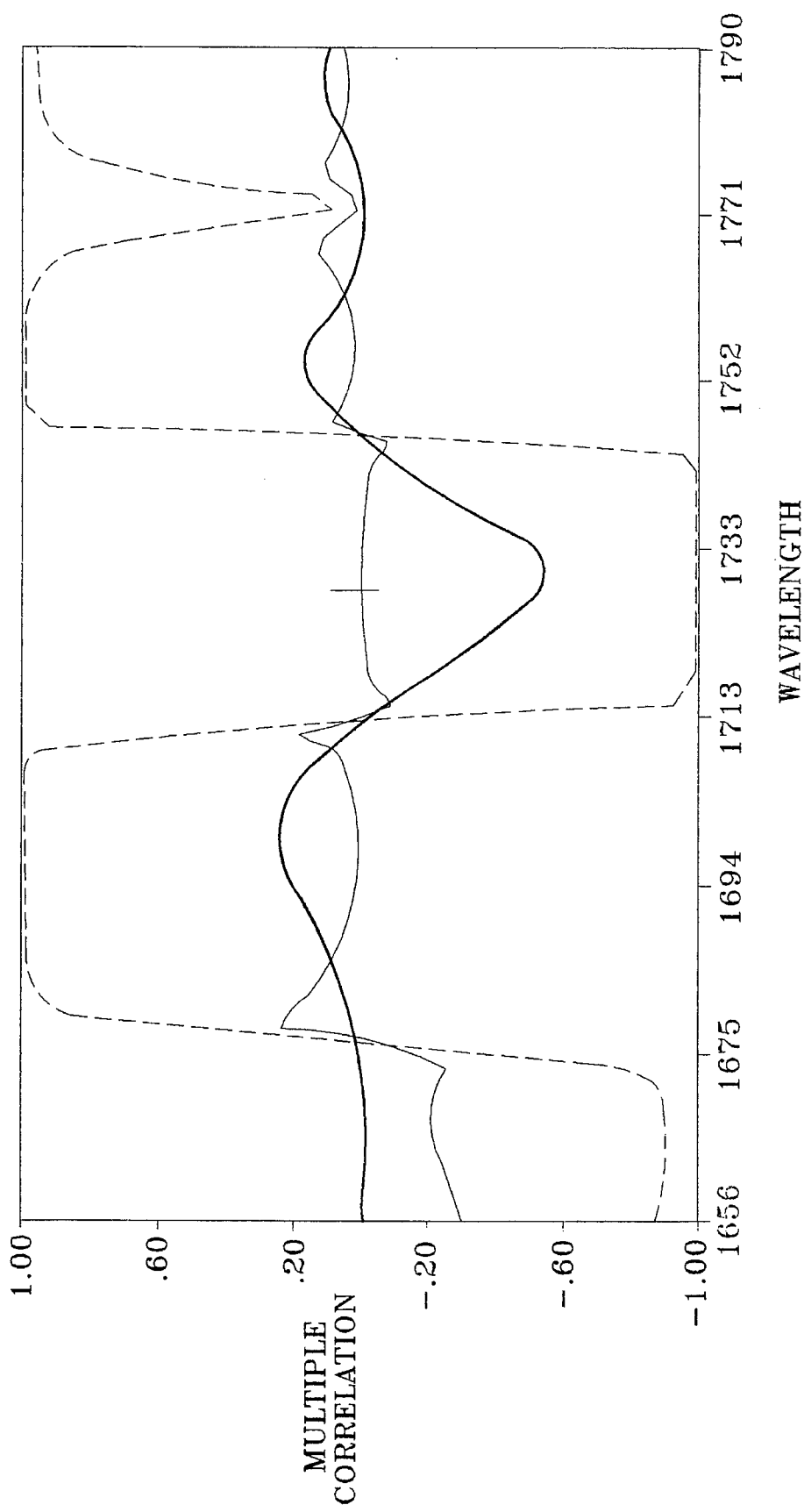
FIG. 8 is a graph illustrating a typical correlation-sensitivity plot of wavelength versus correlation, sensitivity and spectrum data associated with practicing the present invention which illustrates the optimum wavelength region illustrated in FIG. 7.

FIG. 8 is a blown-up section of FIG. 7 illustrating the preferred wavelength range. FIG. 8 better exemplifies the typical correlation-sensitivity plot illustrating the overlaid sensitivity data. The correlation-sensitivity plot illustrated in FIG. 8 shows the wavelength versus correlation, sensitivity and spectrum data. Of particular importance is the illustration of the nonsensitive area of the multiple regression plot around the point of 1728 nanometers.

Figure 9:
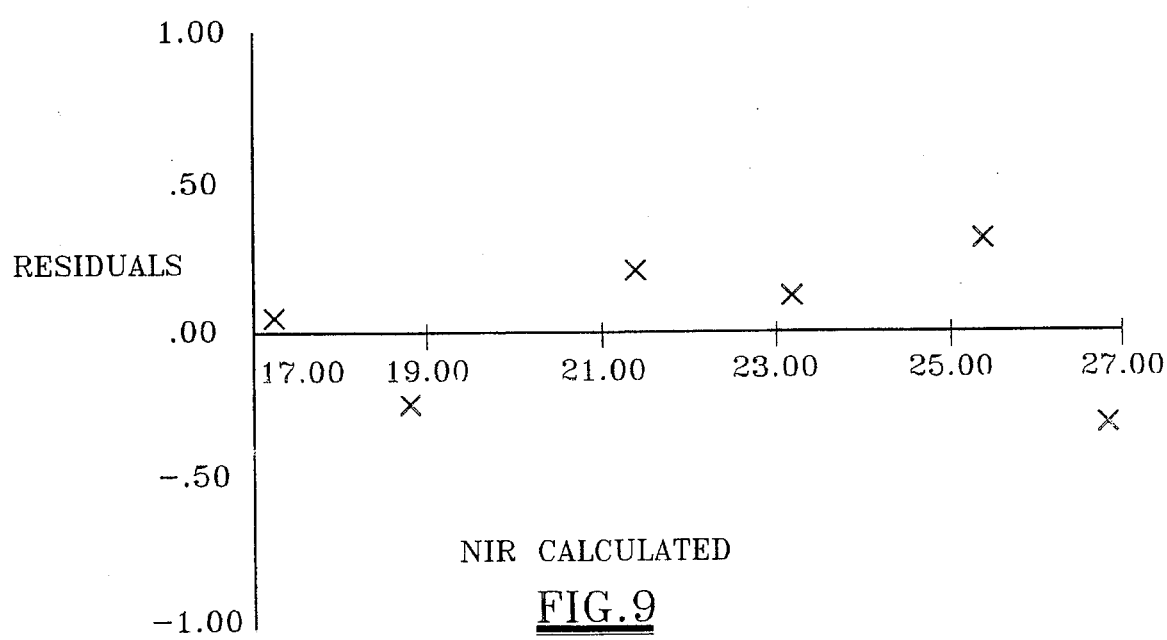
FIG. 9 is a graph illustrating a typical residuals plot of calculated values versus residual data associated with practicing the present invention.

FIG. 9 is a graph illustrating a typical residual plot. The residual plot illustrates the calculated versus the residual data as used for evaluation purposes with the present invention.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A method for determining the concentration of a polymer in a cellulose/polymer mixture, the steps comprising:

(a) acquiring a sample for evaluation from the cellulose/polymer mixture, (b) conditioning the sample to assure it is homogeneous, (c) dewatering the sample to remove excessive liquid therefrom, (d) shredding the sample to assure that the sample is in a fluffed state, (e) scanning the sample to determine the absorption characteristics of the sample, and (f) evaluating the sample absorption to determine the concentration of the polymer in the cellulose/polymer mixture.

2. A method for determining the concentration of a polymer in a cellulose/polymer mixture as defined in claim 1 wherein the step of dewatering the sample to remove excessive liquid comprises the steps of:

(a) engaging the sample with a strained shaker to drain liquid from the sample, (b) engaging the sample with a sample press to drain liquid from the sample, and (c) engaging the sample through a chamois wringer.

3. A method for determining the concentration of a polymer in a cellulose/polymer mixture as defined in claim 2 wherein the step of engaging the sample through a chamois wringer comprises the steps of:

(a) associating the chamois wringer with an absorbing medium, (b) associating the chamois wringer with felt, and (c) applying the sample through the chamois wringer so that the sample engages the absorbing medium and the felt.

4. A method for determining the concentration of a polymer in a cellulose/polymer mixture as defined in claim 1 wherein the step of scanning the sample to determine the absorption characteristics of the sample comprises the step of scanning the sample with a near infrared spectrometer.

5. A method for determining the concentration of a polymer in a cellulose/polymer mixture as defined in claim 1 wherein the step of evaluating the sample to determine the concentration of the polymer in the cellulose/polymer mixture comprises the step of comparing the sample data achieved by scanning the sample with a predetermined calibration data to determine the concentration of the polymer in the cellulose/polymer mixture.

6. A method for determining the concentration of a polymer in a cellulose/polymer mixture as defined in claim 1 wherein the step of acquiring a sample for evaluation further comprises the step of determining the amount of acquired sample to yield a specific volume of desired product.

7. A method for determining the concentration of a polymer in a cellulose/polymer mixture as defined in claim 1 wherein the step of evaluating the sample absorption comprises the step of comparing the sample absorptance with the absorptance of standards representative of known polymer percentages.

8. A method for determining the concentration of a polymer in a cellulose/polymer mixture as defined in claim 7 wherein the step of comparing the sample absorptance with the absorptance of standards representative of known polymer percentages further comprises the step of comparing the respective absorptances between the range of approximately 1630 to 1770 nanometers.

9. A method for determining the concentration of a polymer in a cellulose/polymer mixture as defined in claim 8 wherein the step of comparing the respective absorptances between the range of approximately 1630 to 1770 nanometers further comprises the step of comparing the respective wavelengths at about 1728 nanometers.

10. A method for determining the concentration of a polymer in a cellulose/polymer mixture as defined in claim 1 further comprising, after the step of acquiring a sample, the step of agitating the sample.

11. A method for determining the concentration of a polymer in a cellulose/polymer mixture as defined in claim 1 further comprising, after the step of evaluating the sample absorption, the steps of:

(a) calculating the quantity of additional polymer needed to achieve a desired cellulose/polymer mixture, (b) adding the polymer as needed to the cellulose/polymer mixture, and (c) releasing the resultant cellulose/polymer mixture for use.

12. A method for determining the concentration of a polymer in a cellulose/polymer mixture such that the mixture has characteristic carbon-hydrogen stretching frequencies associated with the mixture, the steps comprising:

(a) dewatering a sample from the cellulose/polymer mixture to remove excessive liquid therefrom, (b) shredding the sample to the extent that the sample is in a fluffed state, (c) scanning the sample using spectroscopy, (d) determining the absorption characteristics of the sample at specific wavelength to generate a sample absorption such that the sample absorption is related to the characteristic carbon-hydrogen stretching frequencies associated with the mixture, (e) comparing the specific sample absorption obtained with standards representative of known polymer percentages, and (f) determining from the comparison the concentration of the polymer in the cellulose/polymer mixture.

13. A method for determining the concentration of a polymer in a cellulose/polymer mixture as defined in claim 12 wherein the step of determining the absorption characteristics of the sample at specific wavelength to generate a sample absorption comprises the step of determining the absorption at a range of approximately 1690 to 1770 nanometers.

14. A method for determining the concentration of a polymer in a cellulose/polymer mixture as defined in claim 12 wherein the step of determining the absorption characteristics of the sample at specific wavelength to generate a sample absorption comprises the step of determining the absorption at a range that falls within the first overtone C–H absorbency range of approximately 1630 to 1750 nanometers.

15. A method for determining the concentration of a polymer in a cellulose/polymer mixture, the steps comprising:

(a) mixing the cellulose/polymer mixture to assure homogeneity, (b) acquiring an appropriate sample, (c) dewatering the sample to remove excessive liquid therefrom, (d) shredding the sample to the extent that the sample is in a fluffed state, (e) evaluating the sample using spectrometry to determine the absorption characteristics of the sample, and (f) comparing the absorption characteristics of the sample with absorption of known polymer percentages to obtain the polymer concentration of the sample, (g) if the polymer content is not acceptable, determining the quantity of additional polymer or cellulose required to add to the mixture to be acceptable and adding the determined amount of polymer or cellulose for the mixture to be acceptable, and (h) if the polymer content is acceptable, releasing the mixture for production.

16. A method for determining the concentration of a polymer in a cellulose/polymer mixture as defined in claim 15 wherein the step of dewatering the sample to remove excessive liquid comprises the steps of:

(a) engaging the sample with a strained shaker to drain liquid from the sample, (b) engaging the sample with a sample press to drain liquid from the sample, and (c) engaging the sample through a chamois wringer.

17. A method for determining the concentration of a polymer in a cellulose/polymer mixture as defined in claim 16 wherein the step of engaging the sample through a chamois wringer comprises the steps of:
(a) associating the chamois wringer with an absorbing medium,
(b) associating the chamois wringer with felt, and
(c) applying the sample through the chamois wringer so that the sample engages the absorbing medium and the felt.

18. A method for determining the concentration of a polymer in a cellulose/polymer mixture as defined in claim 15 wherein the step of evaluating the sample using spectrometry comprises the step of scanning the sample with a near infrared spectrometer.

19. A method for determining the concentration of a polymer in a cellulose/polymer mixture as defined in claim 15 wherein the step of comparing the absorption characteristics of the sample with absorption of known polymer percentages to obtain the polymer concentration of the sample further comprises the step of comparing the respective absorptances between the range of approximately 1630 to 1770 nanometers.

20. A method for determining the concentration of a polymer in a cellulose/polymer mixture as defined in claim 19 wherein the step of comparing the respective absorptances between the range of approximately 1630 to 1770 nanometers further comprises the step of comparing the respective absorptance at about 1728 nanometers.

21. An apparatus for determining the concentration of a polymer in a cellulose/polymer mixture for use in fabricating products therefrom, the apparatus comprising:
(a) means for acquiring a predetermined amount of sample for evaluating the cellulose/polymer mixture such that the sample is calculated to yield a specific weight of desired product,
(b) means for agitating the sample,
(c) means for dewatering the sample,
(d) means for shredding the sample after the sample has been separated into pieces,
(e) a near-infrared spectrometer for evaluating the shredded sample over the range of absorptances which correspond to the absorption characteristics of a desired polymer,
(f) means for determining a specific absorptance within a range which corresponds to a location of maximum absorptance and of low sensitivity with respect to spectral shifts and for calculating a second derivative over the range of absorptances,
(g) means for comparing the specific absorptance determined with standardized absorptances representative of known polymer percentages including comparing the absorbence determined by the second derivative over the range of absorptances associated with the sample to the absorbences determined by a second derivative of known polymer standards bearing specific polymer percentages wherein the comparison is between the range of 1630 to 1770 nanometers, and
(h) means for determining the polymer content by selecting the standardized absorptances which best corresponds to the specific absorptance determined.

22. An apparatus for determining the concentration of a polymer in a cellulose/polymer mixture for use in fabricating products therefrom as defined in claim 21 wherein the means for dewatering the sample comprises further comprising:
(1) a shaker for draining water from the sample,
(2) a sample press for pressing water from the sample, and
(3) a chamois wringer used in association with paper towels and felt for drying the sample.

23. An apparatus for evaluating a desired polymer contained in a cellulose/polymer mixture as defined in claim 21 wherein the means for shredding the sample comprises a blender and associated motor.

24. A method of calibration for use in determining the concentration of a polymer in a cellulose/polymer mixture, the steps comprising:
(a) selecting a plurality of concentrations spread over a preselected concentration range,
(b) preparing a standard sample for each selected concentration,
(c) blending each prepared standard sample with water,
(d) dewatering each blended standard sample,
(e) shredding each dewatered standard sample,
(f) analyzing each shredded standard sample over a range of wavelengths which correspond to the absorption characteristics of a desired polymer to generate spectral absorption data for each sample,
(g) evaluating the respective spectral absorption data to determine maxima and minima absorption values for generating max/min data for each sample,
(h) evaluating the max/min data to determine its appropriateness for use to analyze unknown samples containing a desired polymer, and
(I) selecting the max/min data that corresponds to the desired polymer absorbance and has non-sensitive characteristics.

25. A method of calibration for use in determining the concentration of a polymer in a cellulose/polymer mixture as defined in claim 24 wherein the step of selecting a plurality of concentrations spread over a preselected concentration range comprises selecting five or more selected concentrations differing by approximately two percent.

26. A method for calibration for use in determining the concentration of a polymer in a cellulose/polymer mixture as defined in claim 24 wherein the step of preparing a standard sample for each selected concentration comprises weighing a plurality of portions of dry pulp and weighing a plurality of portions of dry polymer.

27. A method for calibration for use in determining the concentration of a polymer in a cellulose/polymer mixture as defined in claim 24 wherein the step of analyzing each shredded standard sample over a range of wavelengths which correspond to the absorption characteristics of a desired polymer to generate spectral absorption data for each sample comprises analyzing the shredded standard sample over the preselected concentration range for the desired polymer such that the preselected concentration range includes for wavelengths which correspond to the absorption characteristics of the desired polymer for generating spectral absorption data for each shredded standard such that the spectral information is collected on an associated computer, and the analysis comprises obtaining spectral data over a range of 1,100 to 2,500 nanometers and selecting a specific wavelength of approximately 1728 nanometers.

28. A method for calibration for use in determining the concentration of a polymer in a cellulose/polymer mixture as defined in claim 24 wherein the step of evaluating the respective spectral absorption data to determine maxima and minima absorption values for generating max/min data for each sample comprises determining the maxima and minima absorption values for each sample and evaluating same using a second derivative test comprising fitting spectral data over the range of 1,100 to 2,500 nanometers and fitting the spectral data about the 1728 nanometers value.

* * * * *